US00PP31249P3

(12) United States Plant Patent
Hansen

(10) Patent No.: US PP31,249 P3
(45) Date of Patent: Dec. 17, 2019

(54) **X *MANGAVE* PLANT NAMED 'CARNIVAL'**

(50) Latin Name: ***Manfreda* x *Agave* hybrid**
Varietal Denomination: Carnival

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/501,028

(22) Filed: Feb. 11, 2019

(65) Prior Publication Data

US 2019/0254215 P1 Aug. 15, 2019

Related U.S. Application Data

(60) Provisional application No. 62/710,266, filed on Feb. 14, 2018.

(51) Int. Cl.

| | |
|---|---|
| ***A01H 5/00*** | (2018.01) |
| ***A01H 6/12*** | (2018.01) |
| ***A01H 6/00*** | (2018.01) |
| ***A01H 5/12*** | (2018.01) |

(52) U.S. Cl.
USPC ..... Plt./373
CPC ..... *A01H 6/00* (2018.05); *A01H 5/12* (2013.01)

(58) Field of Classification Search
USPC ..... Plt./373
CPC ..... A01H 5/00; A01H 6/12
See application file for complete search history.

*Primary Examiner* — Annette H Para

(57) ABSTRACT

A new and unique X *Mangave* plant named 'Carnival' characterized by long, arching, succulent foliage with blue-green margins and variegated yellowish-cream center developing greyed-purple to cherry red speckling throughout with exposure to high ultraviolet light. The new plant is suitable for the landscape or as a potted plant for the home or the garden.

1 Drawing Sheet

CROSS REFERENCE TO RELATED APPLICATIONS

This application claims the benefit of priority from U.S. Provisional Patent Application No. 62/710,266, filed Feb. 14, 2018, which is incorporated herein by reference in its entirety.

Botanical classification: *Manfreda* x *Agave* hybrid.

Variety denomination: 'Carnival'.

BACKGROUND OF THE INVENTION

The present invention relates to the new and distinct X *Mangave* plant 'Carnival' discovered by the inventor at a wholesale perennial nursery in Zeeland, Mich., USA as an uninduced whole-plant mutation from a proprietary selection from plants originating in a tissue cultured batch of X *Mangave* 'Jaguar' (not patented) in September of 2015. Through trials at the same nursery since that discovery the plant was referred to by the code 13-SP-Mang-285-4. The new plant has been successfully asexually propagated initially by division at the same nursery in Zeeland, Mich. and also by tissue culture. Both methods of asexual propagation systems have been found to produce stable and identical plants that maintain all the unique characteristics of the original plant.

No plants of X *Mangave* 'Carnival' have been sold, in this country or anywhere in the world, prior to the priority date of this application, nor has any disclosure of the new plant been made before the priority date of this application except that which was disclosed within one year of the priority date of this application, and was either derived directly or indirectly from the inventor.

BRIEF SUMMARY OF THE INVENTION

X *Mangave* 'Carnival' differs from its parent, 'Jaguar', as well as all other *Manfreda, Agave* and X *Mangave* known to the applicant. The most similar known X *Mangave* cultivar is 'Kaleidoscope' U.S. Plant Pat. No. 28,614. 'Kaleidoscope' is a similar X *Mangave* sport from the same parent, but the variegation pattern is reversed with the lighter coloration in the margin and the dark green in the center. 'Jaguar' has the habit and shape of the new plant, but the foliage coloration is dark green with burgundy spotting. Other similar X *Mangave* with chimera variegation include: 'Cappuccino' (not patented) with a creamy white center and mahogany-green margin. There are numerous variegated *Agave* known to the inventor including *Agave* 'Dessert Diamond' U.S. Plant Pat. No. 26,384 with a very compact habit and rigid spiny leaves and bright cream margin and medium green leaf centers.

The new plant is unique from all of these variegated *Agave*, X *Mangave* and *Manfreda* known to the inventor by the following combined traits:

1. Long, arching, succulent foliage with blue-green margins and variegated yellowish-green to yellowish cream centers;
2. Foliage develops greyed-purple to cherry-red speckling throughout and strong cherry-red tinting in the center;
3. Moderate growth rate with good natural pup production;

BRIEF DESCRIPTION OF THE DRAWINGS

The photograph of the new plant demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
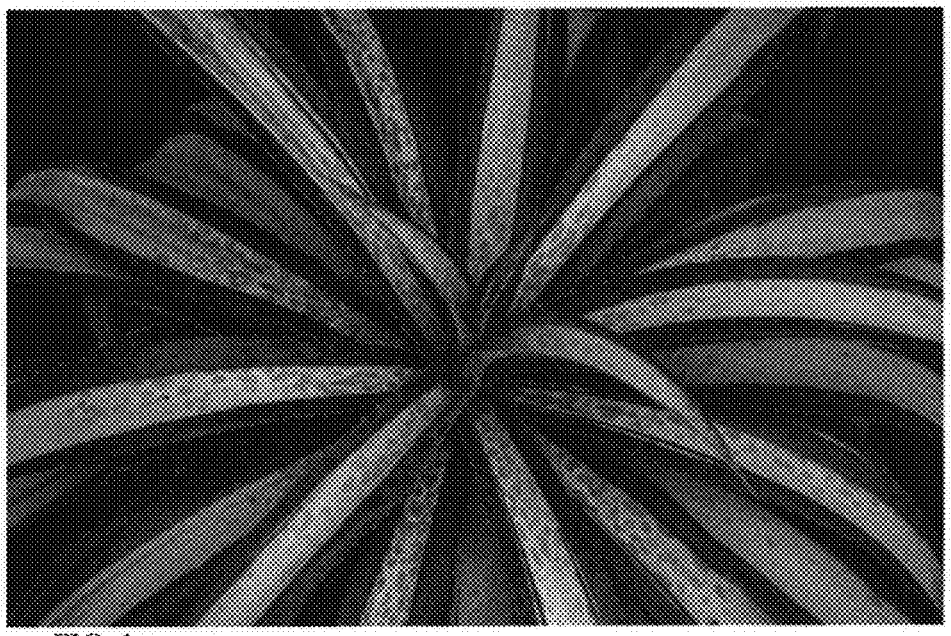
FIG. 1 shows a close-up of the foliage from above.
Figure 2:
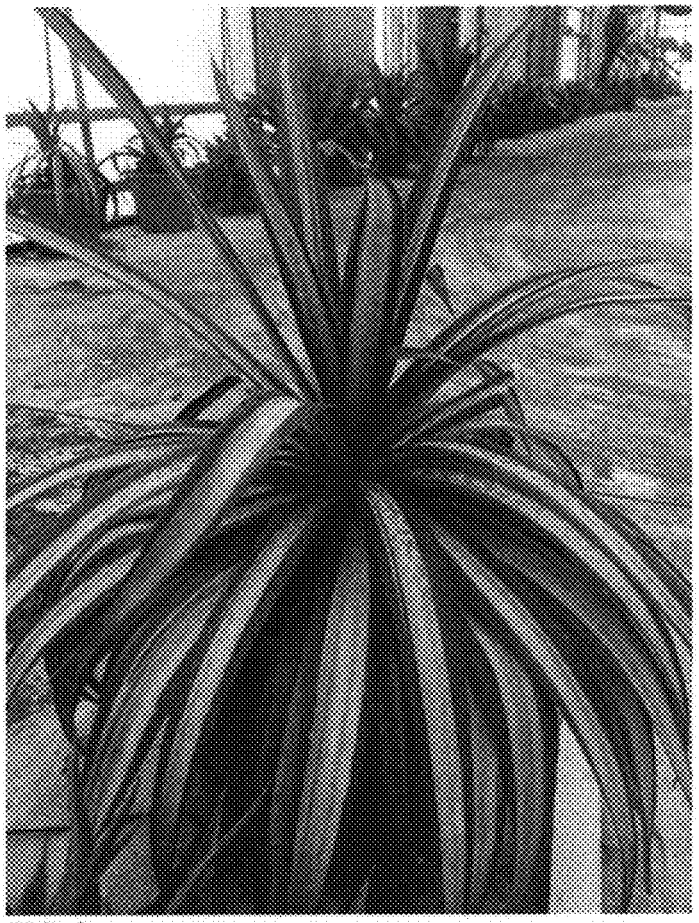
FIG. 2 shows the new plant in a container from the side.

The following descriptions and color references are based on the 2015 edition of The Royal Horticultural Society Colour Chart except where common dictionary terms are used. The new plant, X *Mangave* 'Carnival', has not been observed under all possible environments. The phenotype may vary slightly with different environmental conditions, such as temperature, light, fertility, moisture and maturity levels, but without any change in the genotype. The following observations and size descriptions are of a four-year-old plant in a commercial wholesale greenhouse in Zeeland, Mich. with supplemental water and fertilizer as needed.

Botanical classification: X *Mangave* hybrid;

Variety denomination: 'Carnival';

Sport parentage: Uninduced whole-plant chimeral sport of X *Mangave* 'Jaguar';

Propagation: Division and sterile plant tissue culture;

Time to initiate roots from tissue culture: About 21 days;

Growth rate: Moderate to rapid;

Crop time: About 16 to 20 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of about 60 fleshy leaves radially emerging and arching from central rhizome, producing a symmetrical rounded mound;

Plant size: Foliage height about 42.0 cm tall from soil line to the top of the leaves and about 60.0 cm wide at the widest point at soil line;

Foliage description: Lanceolate; simple, fleshy, glabrous; margins finely dentate with sharp flexible teeth; apex acute with mucro; base truncate, sessile, clasping;

Number of leaves: About 60 per plant;

Leaf dimensions: To about 32.0 cm long, about 5.0 cm wide at base and 3.5 mm thick, average about 30.5 cm long, 4.5 cm wide and 3.5 mm thick; usually bi-laterally symmetrical; glabrous and glaucous above and below; variegation with wide bluish-green margin about 1.0 cm wide at widest portion; with intermediate lighter green zone between margin and center on mature leaves of about 5.0 mm wide at widest point on adaxial surface only; and irregular speckles of between about 1.0 diameter to about 3.0 mm across and about 9.0 mm long, and the yellowish center about 2.3 cm wide;

Foliage fragrance: None observed;

Leaf blade color:

*Adaxial* (*young*) *center.*—Nearest RHS 143C with speckles having undertones of between RHS 174B and RHS 174A.

*Abaxial* (*young*) *center.*—Nearest RHS 143C with speckles having undertones of between RHS 174B and RHS 174A.

*Adaxial* (*young*) *margin.*—A blend between RHS 133A and RHS 139A with speckles of nearest RHS 133A.

*Abaxial* (*young*) *margin.*—A blend between RHS 133A and RHS 139A with speckles of nearest RHS 133A.

*Adaxial* (*mature*) *center.*—Between RHS 4C and RHS 4D with speckles between RHS 186B and RHS 186C.

*Abaxial* (*mature*) *center.*—Nearest RHS 154D with speckles of nearest RHS N187B.

*Adaxial* (*mature*) *margin.*—Blend between RHS 126A and RHS 133A and frequently developing greyed-purple speckles with intense ultra violet light of between RHS N187A and RHS N187B.

*Abaxial* (*mature*) *margin.*—Nearest RHS 136A and frequently developing greyed-purple speckles of nearest RHS N187B to RHS N187A.

*Adaxial intermediate zone.*—Blend between RHS 134B and RHS 137D with speckles of between RHS N187B and RHS N187A.

Apical mucro: Flexible; straight, about 1.0 cm long;

Apical mucro color: Nearest RHS 200A;

Marginal spine: Flexible, glabrous, sharply pointed; color nearest RHS 194C;

Petiole: Sessile;

Veins: Parallel; not distinct;

Inflorescence: Panicle; terete; glaucous; stiff; upright; with about 17 bracts before flowers; to about 167 cm tall and 18.0 mm diameter at base; irregularly branched with branches to about 38 cm long and 3.5 mm diameter at the base;

Peduncle color: Variable; some regions nearest RHS 11D, other regions nearest RHS 4C, with some thin irregular streaking below bracts of nearest RHS 146A; branch color nearest RHS 11D;

Flower bud one day prior anthesis: Clavate; glaucous; apex rounded to broadly acute; base tapered to tube; to about 28.0 mm long, base tube to about 4.5 mm diameter and distal end about 7.0 mm diameter;

Flower bud color: Nearest 146D;

Flower description: Perfect, actinomorphic; about 9.8 cm long and opening to about 4.5 cm across at outside of anthers and across tepals; lasting about 3 to 4 days per flower; flowering period about three weeks in late winter in Michigan greenhouse; producing abundant nectar; approximately 50 flowers per scape; attitude mostly upright;

Flower fragrance: None detected;

Tepals: Six; glaucous abaxial; glabrous both adaxial and abaxial; acute apex and fused base; in two sets of three; outer set about 2.0 cm long and about 6.0 mm wide at fusion; inner set about 1.8 cm long and 5.0 mm wide at base; inner set creased along edge where overlapped with outer set while in bud;

Tepal color: Outer set adaxial blend between RHS N144A and RHS 151C, abaxial nearest RHS 147D with glaucous bloom; inner set adaxial nearest RHS 146A, and abaxial nearest RHS 147D along longitudinal center and between RHS 138B and RHS 138B along creased margin;

Androecium: Six;

*Filaments.*—Six; stiff and straight; about 6.6 cm long and 1.5 mm diameter at base; color nearest RHS N186B.

*Anther.*—Dorsifixed; longitudinal; about 2.4 cm long and 2.0 mm diameter before opening; after dehiscence curving backward; color nearest RHS N186B

*Pollen.*—Abundant; color nearest RHS 13B. .

Gynoecium: Single; about 9.0 cm long;

*Style.*—7.5 cm long and 2.0 mm diameter at base when fully expanded; color maculate; nearest RHS 182D with maculae concentrated distally to nearest RHS 187A.

*Stigma.*—Globose, apex tri-lobed; about 2.5 mm tall and 3.0 mm across top; color side and top blend between RHS 177A and RHS 187A; top stigmatic surface in tri-pointed star with color nearest RHS 194B.

*Ovary.*—Inferior; about 2.3 cm long and 5.0 mm diameter; color nearest RHS 160A.

Fruit: Dehiscent, tri-valved, loculicidal capsule; apex abruptly acute; base slightly tapered; about 3.0 cm long and 1.3 cm across;

Fruit color: When immature nearest RHS 160B; at dehiscence nearest RHS 161B;

Seed: Flattened, near round; about 5.0 mm across and about 1.0 mm thick; color nearest RHS 202A;

Disease resistance: X *Mangave* 'Carnival' has not been observed to be resistant to diseases common to other X *Mangave* beyond that which is normal for *Agave* or *Manfreda*. The plant is xeromorphic and survives well with minimal water once established. Hardiness at least from USDA zone 8 to 11. Full extent of winter hardiness has not been tested.

I claim:

1. A new and distinct cultivar of ornamental X *Mangave* plant named 'Carnival' as herein described and illustrated.

* * * * *